United States Patent
Wallner

(10) Patent No.: US 6,979,697 B1
(45) Date of Patent: Dec. 27, 2005

(54) REGULATION OF SUBSTRATE ACTIVITY

(75) Inventor: Barbara P. Wallner, Cohasset, MA (US)

(73) Assignee: Point Therapeutics, Inc., Boston, MA (US)

( * ) Notice: Subject to any disclaimer, the term of this patent is extended or adjusted under 35 U.S.C. 154(b) by 0 days.

(21) Appl. No.: 09/744,658

(22) PCT Filed: Aug. 13, 1999

(86) PCT No.: PCT/US99/18315

§ 371 (c)(1), (2), (4) Date: May 30, 2001

(87) PCT Pub. No.: WO00/10549

PCT Pub. Date: May 2, 2000

Related U.S. Application Data

(60) Provisional application No. 60/097,376, filed on Aug. 21, 1998.

(51) Int. Cl.[7] .................. A61K 31/00; A61K 31/69; A61K 38/55
(52) U.S. Cl. .................. 514/423; 514/10; 514/19; 514/249; 514/253.09; 514/422
(58) Field of Search .................. 514/10, 19, 249, 514/253.09, 422, 423

(56) References Cited

U.S. PATENT DOCUMENTS

| | | | |
|---|---|---|---|
| 4,935,493 A | 6/1990 | Bachovchin et al. | 530/331 |
| 5,462,928 A | 10/1995 | Bachovchin et al. | 514/19 |
| 5,543,396 A | 8/1996 | Powers et al. | 514/19 |
| 5,965,532 A | 10/1999 | Bachovchin | 514/12 |
| 6,040,145 A | 3/2000 | Huber et al. | 435/7.2 |
| 6,090,786 A | 7/2000 | Augustyns et al. | 514/19 |
| 6,100,234 A * | 8/2000 | Huber et al. | 514/2 |
| 6,258,597 B1 | 7/2001 | Bachovchin et al. | 435/325 |
| 6,300,314 B1 | 10/2001 | Wallner et al. | 514/19 |
| 6,355,614 B1 * | 3/2002 | Wallner | 514/10 |
| 6,503,882 B2 | 1/2003 | Huber et al. | 514/2 |
| 6,548,529 B1 * | 4/2003 | Robl et al. | 514/406 |
| 6,692,753 B2 | 2/2004 | Huber et al. | 424/278.1 |
| 6,703,238 B2 | 3/2004 | Bachovchin et al. | 435/325 |
| 6,770,628 B2 | 8/2004 | Wallner et al. | 514/19 |
| 2003/0158114 A1 * | 8/2003 | Wallner et al. | 514/12 |
| 2003/0199563 A1 * | 10/2003 | Robl et al. | 514/374 |
| 2003/0212044 A1 | 11/2003 | Huber et al. | 514/64 |
| 2004/0077601 A1 | 4/2004 | Adams et al. | 514/64 |
| 2004/0152192 A1 | 8/2004 | Bachovchin et al. | 435/37.2 |

FOREIGN PATENT DOCUMENTS

| | | |
|---|---|---|
| DE | 158109 | 12/1982 |
| DE | 294176 A5 | 9/1991 |
| DE | 294711 A5 | 10/1991 |
| DE | 296075 A5 | 11/1991 |
| DE | 19834591 A1 | 2/2000 |

(Continued)

OTHER PUBLICATIONS

Bristol et al. Inhibition of CD26 . . . Blood. Jun. 15, 1995. vol. 85, No. 12, pp. 3602-3609.*

(Continued)

*Primary Examiner*—Jeffrey Edwin Russel
(74) *Attorney, Agent, or Firm*—Wolf, Greenfield & Sacks, P.C.

(57) ABSTRACT

A method for regulating substrate activity in vivo is useful for the treatment of medical disorders such as inflammation, arteriolosclerosis and angiogenesis. The method involves the administration of an effective amount of a DPP-IV inhibitor to a patient in need of such treatment.

15 Claims, 1 Drawing Sheet

FOREIGN PATENT DOCUMENTS

| | | |
|---|---|---|
| EP | 995440 A1 | 4/2000 |
| EP | 1084705 A2 | 3/2001 |
| WO | WO 91/16339 * | 10/1991 |
| WO | WO 91/16339 A1 | 10/1991 |
| WO | WO 93/08259 * | 4/1993 |
| WO | WO 93/08259 A2 | 4/1993 |
| WO | WO 93/10127 A1 | 5/1993 |
| WO | WO 94/03055 * | 2/1994 |
| WO | WO 94/03055 A1 | 2/1994 |
| WO | WO 95/11689 * | 5/1995 |
| WO | WO 95/11689 A1 | 5/1995 |
| WO | WO 95/15309 * | 6/1995 |
| WO | WO 95/15309 A1 | 6/1995 |
| WO | WO 97/11689 A1 | 4/1997 |
| WO | WO 97/40832 A1 | 11/1997 |
| WO | WO 98/00439 A2 | 1/1998 |
| WO | WO 98/25644 * | 6/1998 |
| WO | WO 98/25644 A1 | 6/1998 |
| WO | WO 98/50046 * | 11/1998 |
| WO | WO 98/50046 A1 | 11/1998 |
| WO | WO 98/50066 A1 | 11/1998 |
| WO | WO 99/28474 * | 6/1999 |
| WO | WO 99/28474 A2 | 6/1999 |
| WO | WO 99/38501 * | 8/1999 |
| WO | WO 99/38501 A2 | 8/1999 |
| WO | WO 99/61431 A1 | 12/1999 |
| WO | WO 99/62914 * | 12/1999 |
| WO | WO 99/62914 A1 | 12/1999 |
| WO | WO 99/67278 A1 | 12/1999 |
| WO | WO 99/67279 A1 | 12/1999 |
| WO | WO 00/10549 A1 | 3/2000 |
| WO | WO 00/56296 A2 | 9/2000 |
| WO | WO 01/14318 A2 | 3/2001 |

OTHER PUBLICATIONS

Shioda et al. Anti-HIV-1 and chemotactic activites. . . PNAS USA. 1998, vol. 95, No. 11, pp. 6331-6336.*

Oravecz et al. Regulation of the receptor specificity. . . J. Exp. Med. 1997, vol. 186, No. 11, pp. 1865-1872.*

Kelly et al. Immunosuppressive Boronic Acid Dipeptides. . . J. Am. Chem. Soc. 1993, vol. 115, pp. 12637-12638.*

Snow et al. Studies on Proline Boronic Acid Dipeptide Inhibitors. . . J. Am. Chem. Soc. 1994, vol. 116, pp. 10860-10869.*

U.S. Appl. No. 60/135,861, filed May 25, 1999.*

Amara et al., HIV coreceptor downregulation as antiviral principle: SDF-1alpha-dependent internalization of the chemokine receptor CXCR4 contributes to inhibition of HIV replication. J Exp Med. Jul. 7, 1997;186(1):139-46.

Arenzana-Seisdedos et al., HIV blocked by chomokine antagonist. Nature. Oct. 3, 1996; 383(6599):400.

Atchison et al., Multiple extracellular elements of CCR5 and HIV-1 entry: dissociation from response to chemokines, Science. Dec. 13, 1996;274(5294):1924-6.

Bachovchin et al., Inhibition of IgA1 proteinases from Neisseria gonorrhoeae and Hemophilus influenzae by peptide prolyl boronic acids. J Biol Chem. Mar. 5, 1990;265(7):3738-43.

Benkirane et al., The cytoplasmic tail of CD4 is required for inhibition of human immunodeficiency virus type 1 replication by antibodies that bind to the immunoglobulin CDR3-like region in domain 1 of CD4. J Virol. Nov. 1995;69(11):6904-10.

Berson et al., A seven-transmembrane domain receptor involved in fusion and entry of T-cell-tropic human immunodeficiency virus type 1 strains. J Virol. Sep. 1996;70(9):6288-95.

Bleul et al., The lymphocyte chemoattractant SDF-1 is a ligand for LESTR/fusin and blocks HIV-1 entry, Nature. Aug. 29, 1996;382(6594):829-33.

Bleul et al., A highly efficacious lymphocte chemattractant, stromal cell-derived factor 1 (SDF-1) J Exp Med. Sep. 1, 1996;184(3):1101-9.

Bristol et al., Inhibition of CD26 enzyme activity with pro-boropro stimulates rat granulocyte/macrophage colony formation and thymocyte proliferation in vitro. Blood. Jun. 15, 1995;85(12):3602-9.

Brubaker et al., Circulating and tissue forms of the intestinal growth factor growth factor, glucagon-like peptide-2. Endocrinology. Nov. 1997;138(11):4837-43.

Brubaker et al., Intestinal function in mice with small bowel growth induced by glucagon-like peptide-2. Am J Physiol. Jun. 1997;272(6 Pt 1):E1050-8.

Coutts et al., Structure-activity relationships of boronic acid inhibitors of dipeptidyl peptidase IV. 1. Variation of the P2 position of Xaa-boroPro dipeptides. J Med Chem. May 10, 1996;39(10):2087-94.

Deacon et al., Dipepidyl peptidase IV inhibition potentiates the insulinotropic effect of glucagon-like peptide 1 in the anesthetized pig, Diabetes. May 1998;47(5):764-9.

Drucker et al., Regulation of the biological activity of glucagon-like peptide 2 in vivo by dipeptidyl peptidase IV. Nat Biotechnol. Jul. 1997;15(7):673-7.

Drucker, Glucagon-like peptides. Diabetes. Feb. 1998;47(2):159-69. Review.

Feil et al., Endothelial cells differentially express functional CXC-chemokine receptor-4 (CXCR-4/fusin) under the control of autocrine activity and exogenous cytokines. Biochem Biophys Res Commun. Jun. 9, 1998;247(1):38-45.

Flentke et al., Inhibition of dipeptidyl aminopeptidase IV (DP-IV) by Xaa-boroPro dipeptides and use of these inhibitors to examine the role of DP-IV in T-cell function. Proc Natl Acad Sci U S A. Feb. 15, 1991;88(4):1556-9.

Hesselgesser et al., Identification and characterization of the CXCR4 chemokine receptor in human T cell lines: ligand binding, biological activity, and HIV-1 infectivity. J Immunol. Jan. 15, 1998;160(2):877-83.

Heveker et al., Dissociation of the signalling and antiviral properties of SDF-1-derived small peptides. Curr Biol. Mar. 26, 1998;8(7):369-76.

Heymann et al., [Has dipeptidyl peptidase IV an effect on blood pressure and coagulation?] Klin Wochenschr. Jan. 2, 1984;62(1):2-10. Review. German.

Hoffmann et al, Dipeptidyl peptidase IV (CD 26) and aminopeptidase N (CD 13) catalyzed hydrolysis of cytokines and peptides with N-terminal cytokine sequences. FEBS Lett. Dec. 20, 1993;336(1):61-4.

Kelly et al., Immunosuppresive boronic acid dipeptides: corrlation between conformation and activity. J Am Chem Soc. 1993; 115(26): 12637-12638.

Kieffer et al., Degradation of glucose-dependent insulinotropic polypeptide and truncated glucagon-like peptide 1 in vitro and in vivo by dipeptidyl peptidase IV. Endocrinology. Aug. 1995;136(8):3585-96.

Kim et al., CK beta-11/macrophage inflammatory protein-3 beta/EBI1-ligand chemokine is an efficacious chemoattractant for T and B cells. J Immunol. Mar. 1, 1998;160(5):2418-24.

Oberlin et al., The CXC chemokine SDF-1 is the ligand for LESTR/fusin and prevents infection by T-cell-line-adapted HIV-1. Nature. Aug. 29, 1996;382(6594):833-5. Erratum in: Nature Nov. 21, 1996;384(6606):288.

Oravecz et al., Regulation of the receptor specificity and function of the chemokine RANTES (regulated on activation, normal T cell expressed and secreted) by dipeptidly peptidase IV (CD26)-mediated cleavage. J Exp Med. Dec. 1, 1997;186(11):865-72.

Reinhold et al., CD26 mediates the action of HIV-1 Tat protein on DNA synthesis and cytokine production in U937 cells. Immunobiology. Jan. 1996;195(1):119-28.

Schall et al., Human macrophage inflammatory protein alpha (MIP-1 alpha) and MIP-1 beta chemokines attract distinct populations of lymphocytes. J Exp Med. Jun. 1, 1993;177(6):1821-6.

Shioda et al., Anti-HIV-1 and chemotactic activities of human stromal cell-derived factor 1alpha (SDF-1alpha) and SDF-1beta are abolished by CD26/dipeptidly peptidase IV-mediated cleavage. Proc Natl Acad Sci U S A. May 26, 1998;95(11):6331-6.

Snow et al., Studies on Proline Boronic Acid Dipeptide Inhibitors of Dipeptidyl Peptidase IV: Identification of a Cyclic Species Containing a B-N Bond. Am J Chem Soc. 1994; 116(24): 10860-10869.

Van Rij et al., The role of a stromal cell-derived factor-1 chemokine gene variant in the clinical course of HIV-1 infection. AIDS. Jun. 18, 1998;12(9):F85-90. Erratum in: AIDS Nov. 8, 2002;16(16):2239.

* cited by examiner

REGULATION OF SUBSTRATE ACTIVITY

RELATED APPLICATIONS

This application is a U.S. National Stage Application under 35 U.S.C. §371 of PCT International application PCT/US99/18315 designating the United States of America, published under PCT Article 21(2) in English, and filed Aug. 13, 1999, which claims the benefit under 35 U.S.C. §119(e) of U.S. provisional application Ser. No. 60/097,376, filed Aug. 21, 1998.

BACKGROUND OF THE INVENTION

This invention relates to inhibitors for dipeptidyl peptidase IV which are used to regulate substrate activity. As used herein, the term "substrate" denotes chemokines, cytokines and biological peptides which are substrates for DPP-IV. This invention also relates to the use of DPP-IV inhibitors in the treatment of medical disorders which may result from the inactivation of substrates implicated in the medical disorder. As used herein, dipeptidyl peptidase IV is alternatively described as "DPP-IV," "DP-IV" and "CD26." CD26 is an ectoenzyme with activity identical to that of DPP-IV.

DPP-IV is a serine type exopeptidase with high substrate specificity cleaves N-terminal dipeptides from proteins if the penultimate amino acid is proline, or in some cases alanine (Fleischer, B. *Immunol. Today* 15:180 (1994)).

A class of low molecular weight synthetic monomeric molecules with high affinity for CD26 have previously been developed and characterized (G. R. Flentke et al., Inhibition of dipeptidyl aminopeptidase IV (DP-IV) by Xaa-boroPro dipeptides and use of these inhibitors to examine the role of DP-IV in T-cell function, *PNAS* (*USA*) 88, 1556–1559 (1991); W. G. Gutheil and W. W. Bachovchin, Separation of L-Pro-DL-boroPro into Its Component Diastereomers and Kinetic Analysis of Their Inhibition of Dipeptidyl Peptidase IV: A New Method for the Analysis of Slow, Tight-Binding Inhibition, *Biochemistry* 32, 8723-8731 (1993)). These molecules have been shown to be potent and specific synthetic inhibitors for CD26-associated DP-IV proteinase activity.

Representative monomeric structures of these transition-state-analog-based inhibitors, Xaa-boroPro, wherein Xaa is an amino acid residue, include Pro-boroPro, Ala-boroPro, Val-boroPro, and Lys-boroPro. BoroPro refers to the analog of proline in which the carboxylate group (COOH) is replaced with a boronyl group [B(OH)$_2$]. Pro-boroPro, the most thoroughly characterized of these inhibitors, has a Ki of 16 picomolar (pM) (W. G. Gutheil and W. W. Bachovchin, supra). Val-boroPro has an even higher affinity, with a Ki of 1.6 pM (W. G. Gutheil and W. W. Bachovchin, supra; R. J. Snow et al., Studies on Proline Boronic Acid Dipeptide Inhibitors of Dipeptidyl Peptidase IV: Identification of a Cyclic Species Containing a B—N Bond, *J. Am. Chem. Soc.* 116, 10860–10869 (1994)). Thus, these Xaa-boroPro inhibitors are about $10^{+6}$ fold more potent than the next best known inhibitors.

U.S. Pat. No. 4,935,493 (Bachovchin '493) and U.S. Pat. No. 5,462,928 (Bachovchin '928), both of which are incorporated herein by reference, disclose protease inhibitors and transition state analogs (the '493 patent) and methods for treating transplant rejection in a patient, arthritis, or systemic lupus erythematosis (SLE) by administering a potent inhibitor of the catalytic activity of soluble amino peptidase activity of dipeptidyl peptidase type IV (G. R. Flentke et al., supra).

Chemokines, or chemoattractant cytokines, are a family of small proteins with a conserved cysteine motifs. These small proteins have been implicated in a wide range of disease states, such as acute and chronic inflammatory processes, angiogenesis, leukocyte migration, regulation of cell proliferation and maturation, hematopoiesis, viral replication, and other immunoregulatory functions. Chemokines are expressed by a number of different cells and have distinct but overlapping cellular targets.

There are two groups of chemokines defined according to their structural characteristics: the CXC and the CC groups. In addition, C-chemokines and CX3C-chemokines have been identified. Members of the CXC group, which include SDF-1 and IL-8, attract mostly neutrophils, while the CC group acts on monocytes and granulocytes. The CC group includes such molecules as human monocyte chemotactic protein 1 (MCP-1) and RANTES. MCP-1 and RANTES are potent direct mediators of the release of histamine by human basophils. Both groups of chemokines are involved in lymphocyte migration to inflammatory sites.

The majority of chemokine receptors are transmembrane spanning molecules which belong to the family of G-protein-coupled receptors. Many of these receptors couple to guanine nucleotide binding proteins to transmit cellular signals. Chemokines and receptor expression is upregulated during inflammatory responses and cellular activation. Chemokines, through binding to their respective receptors, have been shown to be involved in a number of physiologic conditions. For instance, chemokines of the CXC group, like Interleukin-8, can stimulate angiogenesis, while Platelet Factor-4, growth-related oncogene-β (GRO-β) and interferon-γ induced Protein-10 (IP-10) inhibit endothelial cell proliferation and angiogenesis. Interleukin-8 stimulates endothelial cell proliferation and chemotaxis in vitro, and appears to be a primary inducer of macrophage induced angiogenesis. It was shown that the activities of these chemokines are dependent on the NH$_2$-terminal amino acid sequence (Streiter et al., *J. Biol. Chem.*, 270; pages 27348–27357). SDF-1, another CXC chemokine, is active in the recruitment and mobilization of hematopoietic cells from the bone marrow, as well as the attraction of monocytes and lymphocytes. In addition, it interferes with cellular infection of HIV-1 by blocking the interaction of HIV-1 with CXCR-4. As with other chemokines in this group, the amino terminal sequence regulates its activity (Shioda, T., et al., *PNAS*, 95; pages 6331–6336).

Chemokine receptors have been shown to serve not only as receptors to chemokines, but most recently have been identified as receptors for a variety of microbes and the HIV-1 virus. For instance, the Duffy blood group Ag, a chemokine receptor on erythrocytes, is the receptor for the malaria parasite *Plasmodium vivax*, and the platelet activating receptor is a receptor for *Streptococcus pneumonia*.

A number of chemokines, such as RANTES, MIP-1 and SDF-1, or cytokines like IL-2, or peptides like GLP-1, GLP-2, and Substance P, are substrates for DPP-IV. DPP-IV cleaves peptides at the NH$_2$ terminus if the penultimate amino acid is proline. Several cytokines and chemokines have the conserved sequence NH$_2$X-Pro-X, and have been shown to be substrates for DPP-IV. DPP-IV is expressed on the surface of T cells and macrophages. The relationship of CD26 protease activity to its immune function is not clear, however there are indications that cleavage by CD26 of the NH$_2$-dipeptide of several cytokines changes their receptor specificity and/or their functional activities.

Cytokines that are known to be potential substrates for DPP-IV include G-CSF, erythropoietin, IL-1β, IL-2, IL-3, IL-6, IL-11, TNF-β and GM-CSF.

In addition to cytokines and chemokines, a number of biologically active peptides have, on their amino termini, the amino acid sequence Xaa-Pro-Xaa, which serves as the substrate for DPP-IV. Among these are the Glucagon Like Peptides, GLP-1 and GLP-2. GLP-1 is involved in insulin release and glucose uptake, and cleavage by DPP-IV causes inactivation of its activity. Inhibition of DPP-IV will result in the prolonged activation state of this peptide, and represents a therapeutic indication of DPP-IV inhibitors. GLP-2 peptide is involved in intestinal growth and nutrient uptake, and increased activity of GLP-2 will result in an increased nutrient uptake for individuals with intestinal diseases.

In addition to the foregoing, CD26 is known to be highly expressed on hepatosplenic T cell lymphoma, and DPP-IV activity, or the ability of CD26 to bind to collagen fibronectin on the extracellular matrix, may be part of the pathogenic mechanism utilized in by neoplastic cells (Ruiz et al., Cytometry 1998, 34: pages 30–35).

DPP-IV and DPP-II levels are known to be significantly increased in the gingival crevicular fluid of patients with periodontitis. Increased levels of these two proteases seem to be associated with increased attachment loss. It is believed that collagen-CD26 interactions are a part of the pathological observations.

PCT published application WO 95/11689 discloses the use of inhibitors of DPP-IV to block CD26, thereby blocking entry of HIV into CD26-bearing cells. These inhibitors are tetrapeptides having the general formula X-Pro-Y-boroPro where X and Y are chosen from any amino acid. Although the dipeptides are also disclosed, the reference states that dipeptides are unstable, and tetrapeptides are preferred. The inhibitors are used to treat pre-symptomatic HIV-infected patients not by neutralizing the virus, but by blocking viral entry into the cells. The reference does not disclose the effect of DPP-IV inhibition on chemokine activity.

SUMMARY OF THE INVENTION

According to the present invention, a method is provided for the treatment of a medical disorder in a patient which is mediated by substrate activity. Pursuant to this method, a pharmaceutical composition is administered to the patient in an amount which is effective to inhibit DPP-IV activity. This pharmaceutical composition contains, as an active ingredient, a compound represented by the general formula PR, where P is a targeting moiety that binds to DPP-IV, and R is a reactive group that reacts with a functional group in DPP-IV, preferably a reactive center of DPP-IV. Preferably, the active ingredient is a compound comprising an amino group covalently bonded to an alpha-amino boronic acid analog of proline (the term "boroPro" is used herein to designate such an analog having the carboxyl group of proline replaced with a $B(OH)_2$ group, where $(OH)_2$ represents two hydroxyl groups and B represents boron). The active ingredient can therefor be designated as Xaa-boroPro, where Xaa is an amino acid residue. Most preferably, the active ingredient is Val-boroPro wherein the carboxy terminal boroProline is coupled via a peptide linkage in accordance with standard peptide chemistry to a valine amino acid residue.

This active ingredient acts to suppress DPP-IV activity for those substrates which are DPP-IV substrates, resulting in an increase in bioavailability of active chemokine in vivo. The net effect is a positive therapeutic benefit to the patient, particularly with respect to certain disease states, such as inflammation, angiogenesis, arteriolosclerosis, intestinal diseases, diabetes, anorexia, and anti-tumor activity, which could not have been predicted on the basis of current knowledge of DPP-IV activity or inhibition.

Substrates which are applicable to the method of this invention include those which share a conserved $NH_2$-X-Pro sequence (where X is any amino acid or a short peptide). These substrates for DPP-IV, and their activity is altered upon cleavage of the N-terminal sequence. The altered substrates can theoretically possess either enhanced or attenuated activity, but they will most typically be inactivated to some extent. Specific examples of chemokines which are inactivated by DPP-IV include, but are not limited to, SDF-1, RANTES, MIP-3. The inhibition of DPP-IV activity prevents the digestion of chemokines, cytokines and growth factors. The substrates of this invention are implicated in a variety of disease states, including inflammation, arteriolosclerosis, angiogenesis, and anti-tumor activity. Inhibition of DPP-IV by the active compounds of this invention is believed to result in the bioavailability of the substrates for enhancing responses to medical trauma.

The pharmaceutical composition will typically include the active component (preferably Xaa-boroPro, and most preferably Val-boroPro), and a pharmaceutically acceptable carrier. The pharmaceutical composition can also include various adjuvants, enhancers, cytokines, etc., as are known to those skilled in the art. Patient dosages will generally be within the range of 0.001 mg/kg to 100 mg/kg.

DETAILED DESCRIPTION OF THE INVENTION

Figure 1:
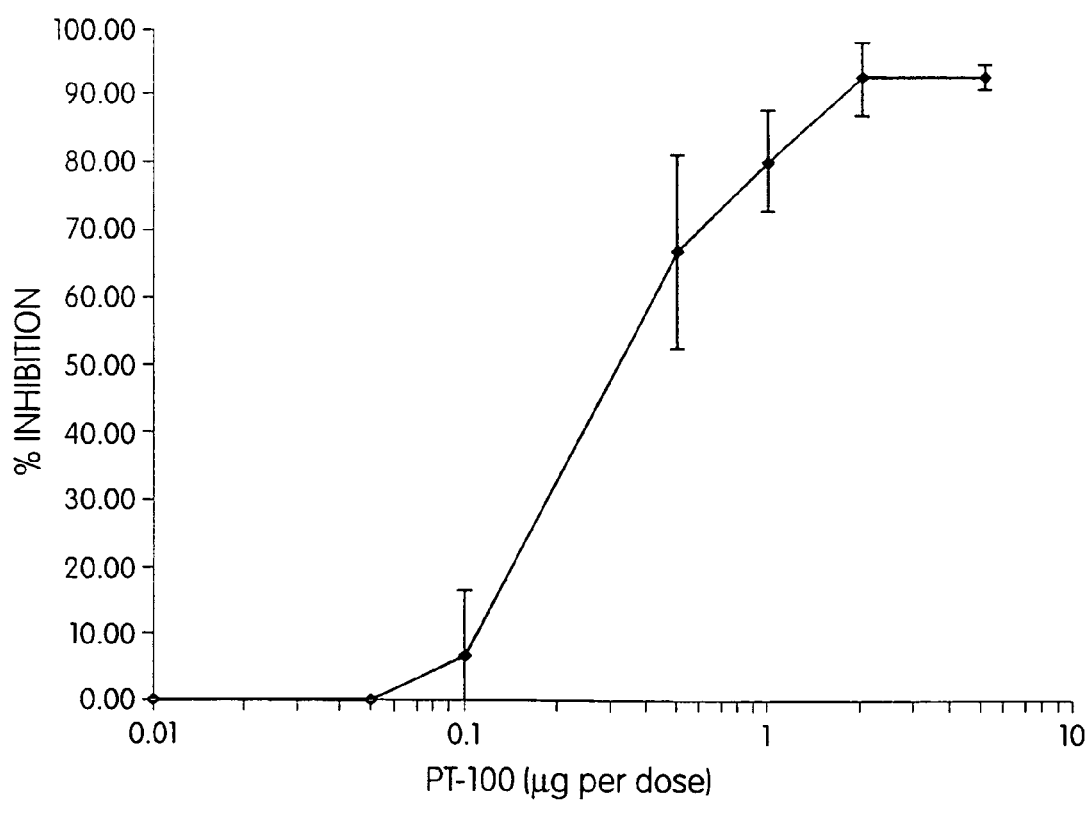
FIG. 1 shows the bioavailability of PT-100 (Val-boroPro), and the HCl and methane sulfonate salts of PT-100.

The invention involves the use of certain compounds to inhibit DPP-IV activity when appropriately administered to a subject. As used herein, the term "subject" is intended to mean a human, non-human primates, dogs, cats, sheep, goats, horses, cows, pigs and rodents. Preferably, the subject is a human patient undergoing medical treatment.

It has now been discovered that inhibition of DPP-IV activity results in the alteration of certain substrates which are implicated in various medical disorders. Since the substrates of this invention are substrates for DPP-IV, it is believed that DPP-IV acts on the substrates in vivo to cleave the two N-terminal sequence where the penultimate amino acid is proline. Alternatively, other peptidases such as peptides A or N could cleave the terminal sequence to expose the Xaa-Pro-Xaa moiety. This cleavage may result in altering the receptor specificity or functionality of the substrate, and typically will result in changes of the activity of the substrate. This may directly effect the patient's response to a particular medical disorder or trauma. For instance, certain chemokines, such as SDF-1, MIP-1 and RANTES, are known to act as attractants for lymphocytes, monocytes, etc. Cleavage of these chemokines by DPP-IV alters their activity and affects the migration of the lymphocytes to the site of an inflammation, hematopoiesis or immune function. The DPP-IV inhibitor acts to block DPP-IV from cleaving the chemokine, either through competitive interaction with DPP-IV or attachment to the active site.

Active Compounds

Compounds useful in the invention include, but are not limited to, compounds that inhibit DPP-IV and are embraced by the formula PR, wherein P represents a targeting moiety that binds to DPP-IV and R represents a reactive group that reacts with a functional group in DPP-IV, preferably a reactive center of DPP-IV. P can be any molecule that binds DPP-IV, including DPP-IV binding molecules embraced by the formula: $D\sim A_1\text{-}A_2\text{-}A_3\text{-}A_4$, wherein D is independently selected from the group consisting of NH and $NH_2$, wherein N represents any isotope of nitrogen, wherein H represents any isotope of hydrogen; "~" independently, is selected from the group consisting of a single bond and a double bond; $A_1$ is selected from the group consisting of a C, a CX and an N, wherein C represents any isotope of carbon, X represents any atom that forms a single bond with carbon; each $A_2$, $A_3$, and $A_4$, independently, is selected from the group consisting of a CX moiety, a CXZ moiety, a CZ moiety, a NX moiety, and an O, wherein X and Z, independently are selected from the group consisting of any atom that forms a single bond and any atom that forms a double bond with C or N and wherein O represent any isotope of oxygen.

Compounds useful according to the invention include the following alternative structures designated as Group I or Group II.

Group I has the structure:

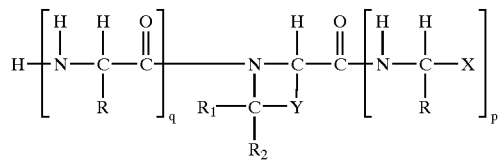

where H represents a hydrogen; C represents a carbon; O represents an oxygen; N represents a nitrogen; each R, independently, is chosen from the group consisting of the R groups of an amino acid, including proline; X represents any atom that forms a single bond with carbon, including hydrogen and halogens; Y is

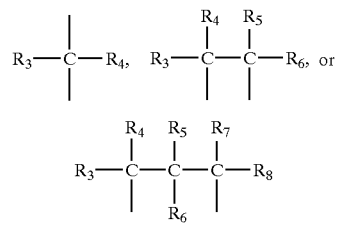

and each $R_1$, $R_2$, $R_3$, $R_4$, $R_5$, $R_6$, $R_7$, and $R_8$, separately is a group which does not significantly interfere with site specific recognition of the inhibitory compound by DPP-IV, and allows a complex to be formed with DPP-IV. Preferably, $R_1$–$R_8$ are H each H represents a hydrogen atom; and q and p are integers which are independently varied between 0 and 4 inclusive.

Alternatively, Group I has the structure:

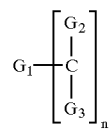

where n is between 0 and 3 inclusive,
each $G_2$ and $G_3$ independently is H or $C_1$–$C_3$ (one to three carbon atoms) alkyl;
$G_1$ is $NH_3$ ($H_3$ represents three hydrogens);
or $G_1$ is

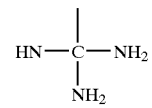

($H_2$ represents two hydrogens),
or $G_1$ is $NG_4$, where $G_4$ is

where $G_5$ and $G_6$ can be NH, H, or $C_1$–$C_3$ alkyl or alkenyl with one or more carbons substituted with a nitrogen. $G_1$ bears a charge, and $G_1$ and $G_2$ do not form a covalently bonded ring structure at pH 7.0.

Group I may also have the structure:

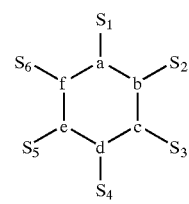

where one or two of the a, b, c, d, e, and f group is N, and the rest are C, and each $S_1$–$S_6$ independently is H or $C_1$–$C_3$ alkyl. Group I may also include a five membered unsaturated ring having two nitrogen atoms, e.g., an imidazole ring.

Group II has the structure:

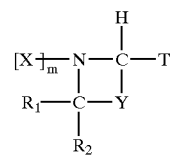

where T is a group of the formula:

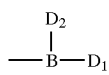

where each $D_1$ and $D_2$, independently, is a hydroxyl group or a group which is capable of being hydrolyzed to a hydroxyl group in aqueous solution at physiological pH;

or T is a group of the formula:

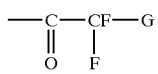

where G is either H, F, or an alkyl group containing 1 to 20 carbon atoms and, optionally, heteroatoms which can be N, S or O;

or T is a phosphonate group of the formula:

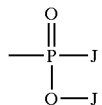

where each J, independently, is any number of N, H, C, O or S atoms, in any combination, or O-alkyl, N-alkyl, or alkyl, each O-alkyl, N-alkyl or alkyl containing 1–20 carbon atoms and, optionally, heteroatoms which can be N, S, or O; or T is

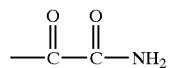

or

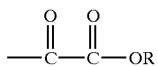

where R is an alkyl, or aryl group and may be substituted or unsubstituted, an alphaketo ester; or

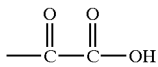

T is generally able to form a complex with the catalytic side of a DPP-IV.

Y is:

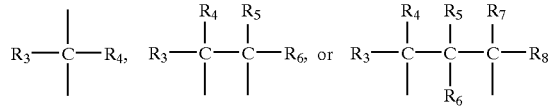

and each $R_1$, $R_2$, $R_3$, $R_4$, $R_5$, $R_6$, $R_7$, and $R_8$, separately is a group which does not significantly interfere with site specific recognition of the inhibitory compound by DPP-IV, and allows a complex to be formed with DPP-IV. Preferably, $R_1$–$R_8$ are H. X is any number of C, H, O, S, or N atoms, in any combination, including any amino acid or organic molecule, and m can vary from 0 to 20.

In preferred embodiments, T is a boronate group, a phosphonate group, a cyano group, or a trifluoroalkyl ketone group; each $R_1$–$R_8$, is H; each $R_1$ and $R_2$ is H, and each Y is $CH_2$—$CH_2$; each R is independently chosen from the R group of proline and alanine; the inhibitory compound has a binding or dissociation constant to DPP-IV of at least $10^{-9}$ M, $10^{-8}$ M or even $10^{-7}$ M; and each D1 and D2 is, independently, F or D1 and D2 together are a ring containing 1 to 20 carbon atoms, and optionally heteroatoms which can be N, S, or O. These compounds are described in U.S. Pat. No. 5,462,928, hereby incorporated by reference.

The more preferred compounds are of the formula:

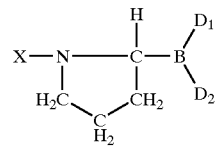

where each $D_1$ and $D_2$, independently, is a hydroxyl group or a group which is capable of being hydrolyzed to a hydroxyl group in aqueous solution at physiological pH; and wherein X is a targeting moiety that mimics the site of a substrate recognized and cleaved by DPP-IV, and preferably is an amino acid, an imino acid, or a peptide which mimics the site of a substrate recognized by a post prolyl cleaving enzyme; C is bonded to B in the L-configuration; and the bonds between B and C, and between Y and N are peptide bonds. By the expression "C is bonded to B in the L-configuration" is meant that the absolute configuration of the C is like that of an L-amino acid.

The active Xaa-boroPro compound of this invention can have an open chain (linear) form or a cyclic form. The linear form can be converted to the cyclic form by a trans to cis isomerization of the proline, and the formation of a new N—B bond. Accordingly, "cyclic form" refers to the cyclized structure of the compounds described in the foregoing formula that are the boron analogs of diketopiperazine.

In a particularly preferred embodiment of the invention, the active compound is an Xaa-boroPro compound, and still more preferably is a Val-boroPro compound. A "Val-boroPro compound" refers to a compound as defined in the formula above in which the carboxy terminal boroPro is covalently coupled via a peptide linkage in accordance with standard peptide chemistry to a valine amino acid residue. In a most preferred embodiment, the compound of the invention is Val-boroPro (also referred to by the manufacturer's designation "PT-100").

The preferred active compounds have targeting moieties that are peptides which mimic the substrate binding site of DPP-IV. Peptide analogs and nonpeptides or peptidomimetics also can be used as targeting moieties. Such molecules can be rationally designed based upon the known sequence of substrates of DPP-IV or can be identified using combinatorial chemistry and screening assays such as are described below.

The development of phage display libraries and chemical combinatorial libraries permits the selection of synthetic compounds which mimic the substrate binding site of a protease such as DPP-IV. Such libraries can be screened to identify non-naturally occurring putative targeting moieties by assaying protease cleavage activity in the presence and absence of the putative phage display library molecule or combinatorial library molecule and determining whether the molecule inhibits cleavage by the protease of its natural substrate or of a substrate analog (e.g., a chromphoric substrate analog which is easily detectable in a spectrophotometric assay). Those phage library and/or combinatorial library molecules which exhibit inhibition of the protease then can be covalently coupled to the reactive groups R disclosed herein and again tested to determine whether these novel molecules selectively bind to the protease (e.g., by repeating the above-noted screening assay). In this manner, a simple, high-through-put screening assay is provided for identifying non-naturally occurring targeting moieties of the invention.

Substrates

The substrates of this invention are those substrates which share a conserved $NH_2$-X-Pro sequence (where X is any amino acid or a short peptide) at the $NH_2$ terminus of the molecule. Substrates having this structural configuration act as substrates for DPP-IV. The inhibitory effect of the present compounds on DPP-IV serves to increase the bioavailability of the substrate in the subject, which in turn results in a positive biological result. For instance, increased bioavailability of selected substrates can produce an increase in immune and antiinflammatory function in the subject. Suitable substrates are known in the art, but until now, no one has correlated the use of DPP-IV inhibitors with a positive medical effect on those conditions which are mediated by the presence and activity of the substrates.

Typical substrates which are the subject of this invention are more fully described below. It should of course be appreciated, however, that other unspecified substrates having conserved $NH_2$-X-Pro sequences, although not specifically described, would also be within the scope of this invention.

SDF-1, or stromal cell-derived factor 1, is a CXC chemokine containing a proline residue at the second position form the N-terminus of the molecule. SDF-1 acts on lymphocytes and monocytes but not neutrophils in vitro, and is an effective and potent mononuclear cell attractant in vivo. SDF-1 is expressed in a broad range of tissues, it may assist in the treatment of arteriolosclerosis, and it also may have anti-HIV activity.

MIP-1 (macrophage inflammatory protein-1) is an attractant for lymphocytes which are essential for immune and inflammatory responses.

RANTES (regulated on activation, normal T-cell expressed and secreted) modulates integrin adhesion and has also been implicated in inflammatory diseases.

GLP-1 (glucagon-like peptide-1) is known to stimulate insulin secretion. This effect is limited in vivo due to the rapid degradation of GLP-1 by DPP-IV. DPP-IV inhibition, using the active compounds of this invention, would potentiate its insulinotropic effects, and may provide assist in the treatment of diabetes.

GLP-2 (glucagon-like peptide-2) is known to stimulate small intestinal growth through the induction of intestinal epithelial proliferation. GPL-2 is also inactivated by DPP-IV in vivo. DPP-IV inhibition may result in increased capacity for nutritional digestion and absorption in vivo, and provide a treatment for AIDS, anemia and anorexia. GLP-2 may be therapeutically useful to enhance mucosal regeneration in patients with intestinal diseases. Inhibition of DPP-IV promotes the absorption of enterostatin and desanginine-enterostatin across rat jejunum.

G-CSF (granulocyte-colony stimulating factor) is a growth factor for hematopoietic cells such as neutrophils.

EPO (erythropoietic-6) is a red blood cell growth factor.

IL-6 (Interleukin-6) is a hematopoietic and lymphocyte growth factor.

IL-11 (Interleukin-11) is a lymphokine.

IL-8 (Interleukin-8) is a hematopoietic growth factor, angiogenesis cytokine.

Substance P is a neuropeptide and a hematopoietic growth factor.

Other suitable chemokines include Substance P, which has vasoactive properties, monomeric fibrin, which effects blood clotting, fibronectin, which promotes binding of hepatocytes and could enhance liver regeneration, MIP-3, a chemoattractant for B-cells, and collagen types I, II, III, and IV, which regulate in part the migration of a number of effector cells, including T cells, across the endothelial barrier.

Similarly, other medical disorders which may be treated according to the method of this invention include allergies, angiogenesis, cardiogenesis, anti-tumor responses, hepatic disease, and organ vascularization.

Substrates not specifically disclosed herein, both known and unknown, which are capable of acting as substrates for DPP-IV, are considered to be fully within the scope of this invention.

Formulation of Pharmaceutical Composition

The compounds of the invention or compositions thereof can be administered alone or in combination with one another, or in combination with other therapeutic agents. For example, treatment with one or more of the compounds of the invention can be combined with more traditional therapies for treating medical disorders, or combined with other cytokines to enhance treatment success.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. The pharmaceutical compositions also may contain, optionally, suitable preservatives, such as: benzalkonium chloride; chlorobutanol; parabens and thimerosal. Carrier formulation suitable for oral, subcutaneous, intravenous, intramuscular, etc., administrations can be found in Remington's Pharmaceutical Sciences, Mack Publishing Co., Easton, Pa.

Routes of Administration

A variety of administration routes are available for treating a subject. The particular mode of delivery selected will depend, of course, upon the particular compound selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes.

Compositions suitable for oral administration may be presented as discrete units, such as capsules, tablets, lozenges, each containing a predetermined amount of the compound of the invention. Other compositions include suspensions in aqueous liquids or non-aqueous liquids such as a syrup, elixir or an emulsion. The oral preparation may include an enteric coating.

As used herein, the term "parenteral" includes subcutaneous, intravenous, intramuscular, or infusion. Compositions suitable for parenteral administration conveniently comprise a sterile aqueous preparation of the compound, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water. Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Intravenous or intramuscular routes are not particularly suitable for long-term therapy and prophylaxis. They could, however, be preferred in emergency situations. Oral administration will be preferred for prophylactic and other treatment because of the convenience to the patient as well as the dosing schedule.

The pharmaceutical compositions may conveniently be presented in unit dosage form and may be prepared by any of the methods well-known in the art of pharmacy. The methods include the step of bringing the compounds of the invention into association with a carrier which constitutes one or more accessory ingredients. In general, the compositions are prepared by uniformly and intimately bringing the compounds into association with a liquid carrier, a finely divided solid carrier, or both, and then, if necessary, shaping the product.

Other delivery systems can include time-release, delayed release or sustained release delivery systems. Such systems can avoid repeated administrations of the compounds described above, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the compound is contained in a form within a matrix such as those described in U.S. Pat. Nos. 4,452,775, 4,667, 014, 4,748,034 and 5,239,660 and (b) diffusional systems in which an active component permeates at a controlled rate from a polymer such as described in U.S. Pat. Nos. 3,832, 253, and 3,854,480. In addition, pump-based hardware delivery systems can be used, some of which are adapted for implantation.

Use of a long-term sustained release implant may be particularly suitable for treatment of chronic conditions. Long-term release, as used herein, means that the implant is constructed and arranged to deliver therapeutic levels of the active ingredient for at least 10 days, and preferably 60 days. Long-term sustained release implants are well-known to those of ordinary skill in the art and include some of the release systems described above.

The compounds described herein are administered in effective amounts. An effective amount is a dosage of the compound sufficient to provide a medically desirable result. The effective amount will vary with the particular condition being treated, the age and physical condition of the subject being treated, the severity of the condition, the duration of the treatment, the nature of the concurrent therapy (if any), the specific route of administration, and like factors within the knowledge and expertise of the health practitioner. An effective amount for stimulating a desired immune response also can be measured, for example, by determining a change in the immune function in a subject (e.g., increased B cell response, increased cytotoxic T cell response, or an ability to slow, halt, or prevent an infection). An effective amount for treating an autoimmune disorder or allergic disorder would be that amount sufficient to lessen or inhibit altogether the immune or allergic response associated with the disorder so as to slow or halt the development of or the progression of the disorder. As used in the claims, "inhibit" embraces all of the foregoing. Likewise, an effective amount for treating an immune system disorder is that amount which can slow or halt altogether the symptoms associated with the immune system disorder so as to prevent the disorder, slow its progression, or halt the progression of the immune system disorder. It is preferred generally that a maximum dose be used, that is, the highest safe dose according to sound medical judgment.

Generally, doses of active compounds will be from about 0.001 mg/kg per day to 1000 mg/kg per day. It is expected that doses range of 0.01 to 100 mg/kg per day will be suitable, preferably orally and in one or several administrations per day. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

All patents, references and other documents that are identified in this patent application are incorporated in their entirety herein by reference.

The following examples are illustrative only and are not intended to limit the invention in any way. A particularly preferred compound of the invention, Val-boroPro ("PT-100"), is used in the examples.

Throughout this application and in particular, in each of the examples, particular embodiments are described and illustrated. It is to be understood that any of the reactive groups disclosed herein can be substituted for the particular reactive groups (e.g., boronyl group) as described in the examples.

EXAMPLE 1

General Synthesis of Active Compounds

Synthesis of the boroPro compounds of this invention are described in Bachovchin '493. In general, the preparatory technique involves straightforward peptide coupling chemistry. The standard peptide coupling chemistry methods and procedures used in this invention are readily available. Examples of books using these methods include, but are not limited to, the following citations incorporated herein by reference: P. D. Bailey, An Introduction to Peptide Chemistry, Ed.: John Wiley & Sons, 1990; Miklos Bodansky, Peptide Chemistry, A Practical Textbook, Ed.: Springer-Verlag, 1988; Miklos Bodansky, Principles of Peptide Synthesis, "Reactivity and Structure Concepts in Organic Chemistry," Volume 16, Ed.: Springer-Verlag, 1984; and Miklos Bodansky, Principles of Peptide Synthesis, "Reactivity and Structure Concepts in Organic Chemistry," Volume 21, Ed.: Springer-Verlag, 1984.

The compounds of the invention can begin with the synthesis of H-boroPro as taught in WO 98/00439. Use of H-boroPro is for illustrative purposes only, and is not intended to limit the scope of this invention.

According to WO 98/00439, H-boroPro was prepared by the synthetic route previously developed and described (G. R. Flentke, et al., "Inhibition of dipeptidyl aminopeptidase IV (DP-IV) by Xaa-boroPro dipeptides and use of these inhibitors to examine the role of DP-IV in T-cell function," PNAS (U.S.A.) 88, 1556–1559 (1991); also described in U.S. Pat. No. 5,462,928). Alternatively, H-boroPro may be produced by a new procedure (Kelly, T. A., et al., "The efficient synthesis and simple resolution of a proline boronate ester suitable for enzyme inhibition studies," Tetrahedron 49, 1009–1016 (1993)). Both of these synthetic routes reportedly yield racemic H-boroPro pinanediol.

According to WO 98/00439, stereochemically pure L, L and L, D diastereomers of Z-Lys-boroPro were prepared by first resolving racemic H-boroPro through crystallization with optically active blocking protecting groups ((1S, 2S, 3R, 5S)-+-pinanediol isomer) followed by coupling the isotopically pure L-boroPro and D-boroPro to the stereochemically pure L isomer of lysine (See U.S. Pat. No. 5,462,928). Alternatively, the L,L and L,D diastereomers of Lys-boroPro were prepared in high optical purity by coupling racemic H-boroPro by L-Lys and separating the resulting diastereomeric Z-Lys-boroPro-diester into its component L,D and L,L diastereomers using reverse phase HPLC as previously described for diastereomeric Pro-boroPro (W. G. Gutheil and W. W. Bachovchin, "Separation of L-Pro-DL-boroPro into Its Component Diastereomers and Kinetic Analysis of Their Inhibition of Dipeptidyl Peptidase IV. A New Method for the Analysis of Slow, Tight-Binding Inhibition," Biochemistry 32, 8723–8731 (1993)).

EXAMPLE 2

Synthesis of Active Cyclic Compounds

In aqueous solution at all pH values, the inhibitors exist as a slowly equilibrating mixture of two conformations: an open chain structure (linear boroProline compound) which is inhibitory (active species), and a cyclic structure (cyclic boroProline compound) which is non-inhibitory (inactive species). The open, active, inhibitory chain species is favored at low pH while the cyclized structure is favored at neutral pH. The reaction is fully reversible: the open chain becomes predominant at low pH. The open chain to cyclic species reaction involves a trans to cis isomerization of the proline and the formation of a new N—B bond. The cyclized structure is the boron analog of a diketopiperazine, a product often seen in peptide chemistry. Cyclization liberates one equivalent of H+ thereby explaining the requirement for base in the cyclization reaction and acid in the opening reaction. The cyclic structure is quite stable in aqueous solutions of high pH.

Prolonged incubation at high pH does not lead to the complete disappearance of DPP-IV inhibitory activity for any of the Xaa-boroPro compounds examined. This observation was the first evidence that the active inhibitor was in a conformation equilibrium with a non-inhibitory species rather than undergoing an irreversible inactivation. The half life for the reformation of the open chain species from the cyclic structure is surprisingly low. Thus, it was concluded that the loss of inhibitory activity in aqueous solution was due to a pH dependent conformational equilibrium rather than a degradation reaction.

The fact that the inhibitory activity does not go to zero for any of the Xaa-boroPro inhibitors, even after prolonged incubation, together with the fact that the reverse reaction, i.e., cyclic to open chain is slow, suggested that it should be possible to measure the equilibrium constant for the conformation equilibrium by measuring the apparent Ki at equilibrium and comparing it with the true Ki. It has been reported that the ratio of [cyclic]: [open] forms, at neutral pH, is 156:1 for Pro-boroPro and 11130:1 for Val-boroPro (W. G. Gutheil and W. W. Bachovchin, Separation of L-Pro-DL-boroPro into Its Component Diastereomers and Kinetic Analysis of Their Inhibition of Dipeptidyl Peptidase IV. A New Method for the Analysis of Slow, Tight-Binding Inhibition, Biochemistry 32, 8723–8731 (1993)). This means that less than 1% Pro-boroPro and less than 0.1% of Val-boroPro exists as the open chain, inhibitory species, at equilibrium at pH 7.0. Nevertheless, under these conditions the inhibitors behave as though they had Ki's of 2.5 nM and 1.8 nM respectively. This apparent Ki of the "fully inactivated" species is still substantially better than, (~1000-fold) that of other inhibitors of DPP-IV thus far reported.

The inventors believe that the cyclic compounds of the invention have the ability to specifically bind to CD26. Accordingly, the inventors predict that the biological function of the compounds of the invention could be significantly increased (approximately 100–1000 times) by orally administering the cyclic compounds of the invention and permitting the conformational changes, e.g., linearization, to occur in vivo (e.g., under the acidic conditions of the stomach).

Thus, if linearization is necessary, it can be accomplished in vivo and therefore, therapeutic concentrations in the systemic circulation can be generated in situ and, accordingly, it is believed that the bioactivity of the compounds of the invention can be increased by approximately 100–1000 fold. In addition, it is believed that the cyclic boroProline compounds of the invention, in lyophilized or solid form, have improved shelf life properties, thereby contributing to the further utility of the compounds of the invention.

Each of the compounds prepared as described above can be purified to homogeneity using HPLC and its identity can be confirmed by NMR spectroscopy, amino acid composition, or mass spectroscopy as deemed necessary.

The cyclic compounds of the invention can be converted to linear form by adjusting the pH to an acidic pH (e.g., pH range: 1–3) and the potency of inhibition of CD26 proteinase activity by the linear boroProline compounds can be determined using conventional enzyme analysis (example provided below). In addition, the immunomodulatory effects of the compounds of the invention are evaluated by in vivo experiments using animal models and by in vitro experiments using cell culture methods that are believed by those of ordinary skill in the art to be predictive of an in vivo activity.

EXAMPLE 3

Assessment of Functional Activity

The compounds of the invention have at least the following properties: (I) binding site is the DPP-IV active site; and (ii) exhibit cross-species specificity.

The assays which are used to assess functional activity include: DPP-IV activity, oral and subcutaneous bioavailability assays, and are described below.

EXAMPLE 4

Measuring Standard DPP-IV Activity

Assays to measure DPP-IV activity can be performed on the compounds of the invention. Methods for quantitatively measuring the interaction of small peptidomimetic inhibitors with DPP-IV, as well as for the interaction of CD26 with larger ligands, e.g., the HIV Tat protein, have been developed (W. G. Gutheil and W. W. Bachovchin. Separation of L-Pro-DL-boroPro into Its Component Diastereomers and Kinetic Analysis of Their Inhibition of Dipeptidyl Peptidase IV. A New Method for the Analysis of Slow, Tight-Binding Inhibition, *Biochemistry* 32, 8723–8731 (1993); Gutheil, W. G., and W., B. W. Kinlsq, A Matlab Program for Fitting Kinetics Data with Numerically Integrated Rate Equations and Its Application to the Analysis of Slow, Tight Binding Data, *Analytical Biochemistry* 223, 13–20 (1994); Gutheil, W. G., et al., HIV-1 Tat Binds to DP IV (CD26): A possible Mechanism for Tat's Immunosuppressive Activity, *Proc. Natl. Acad. Sci. U.S.A.* 91, 6594–6598 (1994)). These methods use the chromatogenic substrate Ala-Pro-p-nitroanilide (AppNA) and fluorescent substrate Ala-Pro-7-amino-4-trifluoromethyl coumarin (AP-AFC). AppNA and AP-AFC are commercially available (e.g., Enzyme Systems Products, Dublin, Calif.).

EXAMPLE 5

Measuring Oral Bioavailability

An in vitro assay of serum DPP-IV activity has been developed, which can be used as a surrogate marker to determine the bioavailability of PT-100 in serum following subcutaneous or oral administration in mice. This assay is based on the ability of PT-100 to inhibit serum DDP-IV protease activity in a dose dependent manner.

As shown in FIG. 1, mice received PT-100 at indicated doses by gavage. Blood samples are taken two hours post administration and serum DPP-IV activity is determined. DPP-IV activity is measured in a fluorometric assay using the synthetic substrate 7-amino-4-trifluoromethyl coumarin (AFC)-AlaPro (15). Total inhibition of serum DPP-IV activity is achieved at doses of 2 µg or 5 µg PT-100. Doses below 2 µg result in a dose dependent decrease of DPP-IV inhibition.

While the invention has been described with respect to certain embodiments, it should be appreciated that many modifications and changes may be made by those of ordinary skill in the art without departing from the spirit of the invention. It is intended that such modifications, changes and equivalents fall within the scope of the appended claims.

What is claimed is:

1. A method for treating a medical disorder in a subject mediated by the alteration of substrate activity comprising administering to the subject an effective amount of a compound having the formula

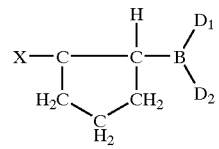

wherein each $D_1$ and $D_2$ is a hydroxyl group or a group which is capable of being hydrolyzed to a hydroxyl group in aqueous solution at physiological pH; wherein X is an amino acid; and wherein C is bonded to B in the L-configuration, said amount being sufficient to prevent chemokine alteration by inhibiting DPP-IV activity, and wherein the medical disorder is selected from the group consisting of arteriolosclerosis and insufficient blood clotting.

2. The method of claim 1 wherein the compound is Val-boroPro.

3. The method of claim 1 wherein the compound is cyclic X-boroPro.

4. The method of claim 1 wherein the substrate is selected from the group consisting of SDF-1, RANTES, MIP-1, MIP-3, GLP-2, G-CSF, EPO, IL-6, IL-11, IL-8, Substance P, fibronectin, and monomeric fibrin.

5. The method of claim 1 wherein the compound is given to the subject by oral administration.

6. The method of claim 1 wherein the compound is given to the subject by parenteral administration.

7. The method of claim 1 wherein the effective amount is in the range of 0.01 mg/kg per day to 100 mg/kg per day.

8. The method of claim 1 wherein the compound has a binding or dissociation constant to DPP-IV of at least $10^{-9}$ M.

9. A method for treating an intestinal disease consisting of administering to a subject in need thereof an effective amount of a compound having the formula

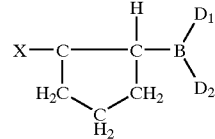

wherein each $D_1$ and $D_2$ is a hydroxyl group or a group which is capable of being hydrolyzed to a hydroxyl group in aqueous solution at physiological pH, X is an amino acid, and C is bonded to B in the L-configuration, said amount being sufficient to prevent chemokine alteration by inhibiting DPP-IV activity, and a pharmaceutically acceptable carrier, wherein the intestinal disease is not a cancer, tumor or neoplasm.

10. The method of claim 9 wherein the compound is Val-boroPro.

11. The method of claim 9 wherein the compound is cyclic X-boroPro.

12. The method of claim 9 wherein the compound is given to the subject by oral administration.

13. The method of claim 9 wherein the compound is given to the subject by parenteral administration.

14. The method of claim 9 wherein the effective amount is in the range of 0.01 mg/kg per day to 100 mg/kg per day.

15. The method of claim 9 wherein the compound has a binding or dissociation constant to DPP-IV of at least $10^{-9}$ M.

* * * * *